US010239819B2

(12) United States Patent
Abraham et al.

(10) Patent No.: US 10,239,819 B2
(45) Date of Patent: Mar. 26, 2019

(54) METHODS FOR PRODUCING AN ESTER OF AN ALPHA, BETA-UNSATURATED CARBOXYLIC ACID

(71) Applicant: CARGILL, INCORPORATED, Wayzata, MN (US)

(72) Inventors: Timothy Walter Abraham, Minnetonka, MN (US); Ravi R. Gokarn, Omaha, NE (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

(21) Appl. No.: 15/518,373

(22) PCT Filed: Oct. 15, 2015

(86) PCT No.: PCT/US2015/055744
§ 371 (c)(1),
(2) Date: Apr. 11, 2017

(87) PCT Pub. No.: WO2016/061356
PCT Pub. Date: Apr. 21, 2016

(65) Prior Publication Data
US 2017/0313644 A1 Nov. 2, 2017

Related U.S. Application Data
(60) Provisional application No. 62/065,446, filed on Oct. 17, 2014.

(51) Int. Cl.
C07C 67/327 (2006.01)
C07C 67/54 (2006.01)
C07C 67/03 (2006.01)

(52) U.S. Cl.
CPC ............ *C07C 67/327* (2013.01); *C07C 67/03* (2013.01); *C07C 67/54* (2013.01)

(58) Field of Classification Search
CPC .................................................. C07C 67/327
See application file for complete search history.

(56) References Cited

U.S. PATENT DOCUMENTS

| | | |
|---|---|---|
| 2,379,625 A | 7/1945 | Coes |
| 2,469,701 A | 5/1949 | Redmon et al. |
| 2,859,240 A | 11/1958 | Holmen |
| 3,590,073 A | 6/1971 | Carr et al. |
| 3,619,397 A | 11/1971 | Jacquemet |
| 3,639,466 A | 2/1972 | Leichtle |
| 3,699,059 A | 10/1972 | Smeets |
| 3,875,212 A | 4/1975 | Ohrui et al. |
| 3,954,854 A * | 5/1976 | Gehrmann ............ C07C 51/487 562/599 |
| 4,187,300 A | 2/1980 | Kinnamon |
| 4,211,846 A | 7/1980 | Lafferty |
| 4,729,978 A | 3/1988 | Sawicki |
| 4,786,756 A | 11/1988 | Paparizos et al. |
| 4,792,620 A * | 12/1988 | Paulik ............... B01J 31/0231 560/232 |
| 4,937,359 A | 6/1990 | Seebach et al. |
| 4,970,334 A | 11/1990 | Argyropoulos et al. |
| 5,132,456 A | 7/1992 | King et al. |
| 5,294,720 A | 3/1994 | Jadhav et al. |
| 5,371,273 A | 12/1994 | Shima et al. |
| 5,439,674 A | 8/1995 | Noda et al. |
| 5,659,029 A | 8/1997 | Ellis et al. |
| 5,739,379 A | 4/1998 | Shima et al. |
| 6,803,217 B2 | 10/2004 | Moore et al. |
| 6,902,917 B1 | 6/2005 | Moore et al. |
| RE39,333 E | 10/2006 | Nishiyama et al. |
| 7,186,541 B2 | 3/2007 | Buckel et al. |
| 7,652,167 B2 | 1/2010 | Lira et al. |
| 7,737,296 B2 | 6/2010 | Kozono et al. |
| 7,999,130 B2 * | 8/2011 | Ackermann ............ C07C 51/09 560/129 |
| 8,338,145 B2 | 12/2012 | Tsobanakis et al. |
| 9,012,685 B2 | 4/2015 | Gwak et al. |
| 2001/0008736 A1 | 7/2001 | Fanta et al. |
| 2002/0055650 A1 | 5/2002 | Hidaka et al. |
| 2004/0210087 A1 | 10/2004 | Meng et al. |
| 2005/0221457 A1 | 10/2005 | Tsobanakis et al. |
| 2005/0222456 A1 | 10/2005 | Brands et al. |
| 2005/0222458 A1 | 10/2005 | Craciun et al. |
| 2006/0041165 A1 | 2/2006 | Tretjak et al. |

(Continued)

FOREIGN PATENT DOCUMENTS

| | | |
|---|---|---|
| DE | 3222837 A1 | 12/1983 |
| GB | 744582 A | 2/1956 |

(Continued)

OTHER PUBLICATIONS

Zaragoza Dorwald (Side Reactions in Organic Synthesis, 2005, WILEY-VCH Verlag GmbH & Co. KGaA, Weinheim, Preface. p. IX (Year: 2005).*
"Aldrich Chemical Co., Inc.", Catalog, p. 961 (1996).
"Classification Table of Catalysts for Reactions, published by Kagaku Kogyo, edited by Taruma Lab, Kyoto University", ISDN: 3058-09019-0915, 173-178.
"Industrial Catalytic Reaction I, edited by Kodansha Scientific, Published by Kodansha Ltd.", ISBN: 4-06-191408-1(0), 9 page.
Bartoli, et al., "An Efficient Procedure for the Diasteroselective Dehydration of β-Hydroxy Carbonyl Compounds by CeCl 3 7H 2 O/Nal System", Organic Letters, vol. 2, No. 13, 2000, 1791-1793.
Chattopadhyay, et al., "Enzymatic Esterification of 3-Hydroxybutyric Acid", Biotechnology Letters, vol. 15, Issue 3, Mar. 1993, 245-250.
D. Pressman and H. J. Lucas, "Hydration of Unsaturated Compound XI, Acrolein and Acrylic Acid", Journal of the American Chemical Society, Aug. 1942, 1953-1957.

(Continued)

*Primary Examiner* — Paul A Zucker

(57) ABSTRACT

A method for producing esters of an alpha, beta-unsaturated carboxylic acid are disclosed, the method includes reacting a three or four carbon beta-hydroxyalkanoate composition or mixtures thereof with a mono-alcohol under heating conditions to form a reaction product and distilling the reaction product to recover a composition containing at least fifty percent by weight of the ester of the alpha, beta-unsaturated carboxylic acid.

19 Claims, No Drawings

(56) References Cited

U.S. PATENT DOCUMENTS

| | | | |
|---|---|---|---|
| 2007/0191629 A1 | 8/2007 | Chen et al. | |
| 2009/0298144 A1* | 12/2009 | Tsobanakis et al. | C07C 51/377 435/135 |
| 2010/0113822 A1 | 5/2010 | Craciun et al. | |
| 2010/0273224 A1 | 10/2010 | Joachim et al. | |
| 2011/0125118 A1 | 5/2011 | Lynch et al. | |
| 2011/0160480 A1 | 6/2011 | Hottois et al. | |
| 2012/0142945 A1 | 6/2012 | Hwang et al. | |
| 2013/0150616 A1 | 6/2013 | Tsobanakis et al. | |
| 2013/0281649 A1 | 10/2013 | Yoshida et al. | |
| 2013/0345470 A1 | 12/2013 | Tengler et al. | |
| 2016/0229787 A1 | 8/2016 | Edgar et al. | |
| 2016/0272569 A1 | 9/2016 | Abraham et al. | |

FOREIGN PATENT DOCUMENTS

| | | |
|---|---|---|
| GB | 1082179 A | 9/1967 |
| JP | 9143126 A | 3/1979 |
| JP | 56021593 A | 2/1981 |
| JP | 58-158189 A | 9/1983 |
| JP | 60078941 A | 5/1985 |
| JP | 63188650 A | 8/1988 |
| JP | 63313739 A | 12/1988 |
| JP | 7017909 A | 1/1995 |
| JP | 09132555 A | 5/1997 |
| JP | 2000319227 A | 11/2000 |
| WO | 0116346 A1 | 3/2001 |
| WO | 02090312 A1 | 11/2002 |
| WO | 2003082795 A2 | 10/2003 |
| WO | 2013134385 A1 | 9/2013 |
| WO | 2015058116 A1 | 4/2015 |
| WO | 2015058118 A1 | 4/2015 |
| WO | 2016061356 A1 | 4/2016 |

OTHER PUBLICATIONS

Hasegawa, et al., "Production of beta-Hydroxypropionic Acid from Propionic Acid", Journal of Fermentation Technology, vol. 60, No. 6, Dec. 1982, 591-594.

Kissa, et al., "Solubility of Alkali Metal Carboxylates in Hydrocarbons", Journal of Colloid Science, vol. 17, No. 9, Dec. 1962, 857-864.

Levene, et al., "The Configurational Relationships of 2-Hydroxy, 3-Hydroxy and 4-Hydroxy Acids", Journal of Biological Chemistry, vol. 69, Apr. 1926, 165-173.

Lira, et al., "Ind. Eng. Chem. Res.(1993) 32: 02608-2613".

Mats From, et al., "Lipase catalyzed esterification of lactic acid", Biotechnology Letters, vol. 19, Issue 4, Apr. 1997, 315-318.

Morrison, et al., "Organic Chemistry", vol. 1, Fourth edition, 1983, 423 Pages.

Odell, et al., "Hydrothermal reactions of lactic acid catalysed by group: VIII Metal complexes", Journal of Organometallic Chemistry, vol. 290, Issue 2, Jul. 23, 1985, 241-248.

Rimenschneider, et al., "Ullmann's Encyclopedia of Industrial Chemistry", Fifth Edition, 1999 Electronic Release, 1994, pp. 181, 196 and 199.

Riemenschneider, et al., "Ullmann's Encyclopedia of Industrial Chemistry", Sixth Edition, 1999 Electronic Release, 1999, Wiley-VCH, Weinheim, Germany, XP002247378 Esters, Organic Production.

Seo, et al., "Kinetics of Esterfication of Lactic Acid and Methanol in the Presence of Cation Exchange Resin Using a Pseudo-Homogenous Model", Journal of Chemical Engineering of Japan, vol. 33, No. 1, (2000)., 2000, pp. 128-133.

Sharma, et al., "Journal of Molecular Catalysis B: Enzymatic, 10(5)", 531-534.

Van Der Baan, et al., "Synthesis of β-Hydroxy Esters by Lithium/Ammonia Rejection of a β-Epoxy Esters", Synthesis, vol. 10, Oct. 1990, 897-899.

W.A. Drushel, et al., "On the Preparation and Hydrolysis of Ethyl Hydracrylate", American Journal of Science, vol. 39, 1915, 113-121.

* cited by examiner

METHODS FOR PRODUCING AN ESTER OF AN ALPHA, BETA-UNSATURATED CARBOXYLIC ACID

CROSS-REFERENCE TO RELATED APPLICATIONS

This application is a national phase application of international application PCT/US2015/055744, filed Oct. 15, 2015, and entitled METHODS FOR PRODUCING AN ESTER OF AN ALPHA, BETA-UNSATURATED CARBOXYLIC ACID, which application claims the benefit of U.S. Provisional Application 62/065,446 filed on Oct. 17, 2014, and entitled METHODS FOR PRODUCING AN ESTER OF AN ALPHA, BETA-UNSATURATED CARBOXYLIC ACID, which applications are hereby incorporated by reference in their entirety.

TECHNICAL FIELD

The present disclosure generally relates to methods and systems for producing esters of alpha-beta unsaturated carboxylic acids from beta-hydroxy carboxylic acid recovery bottoms.

BACKGROUND

During the production and purification process of a beta-hydroxycarboxylic acid, for example 3-hydroxypropionic acid, the beta-hydroxycarboxylic acid may be evaporated or distilled from less-volatile compounds present in a partially purified fermentation broth. These less-volatile components, which contain significant amounts of beta-hydroxycarboxylic acid in the form of oligomers of beta-hydroxycarboxylic acid and saccharide esters, are purged out of the system as waste and may incur a significant yield loss of the beta-hydroxycarboxylic acid, as well as a solid waste disposal costs.

SUMMARY

In the embodiments, the beta-hydroxyalkanoate typically comprises a three or four carbon beta-hydroxyalkanoate, for example 3-hydroxypropionic acid ("3-HP"), 3-hydroxybutyric acid ("3-HB"), and 3-hydroxyisobutyric acid ("3-HIB"). Typically, the mono-alcohol comprises C1 to C6 monoalcohols, (for example, methanol, ethanol, propanol, or butanol). For ease of manufacture with readily available materials and to obtain esters having particularly beneficial functional properties ethanol or butanol are typically utilized. The ester of the alpha-beta unsaturated carboxylic acid typically comprises alkyl acrylates and alkyl methacrylates, wherein the alkyl group typically is derived from methanol, ethanol, propanol, butanol and pentanol. For acrylate esters, butanol and ethanol are often the preferable mon-alcohols to be utilized.

DETAILED DESCRIPTION

"Free beta-hydroxyalkanoate" is measured and determined using similar methods as those described for analyzing and determining free acidity in Holten, C. H. *Lactic Acid—Properties and Chemistry of Lactic Acid and Derivatives*, Verlag Chemie (1971): pp. 199-203. An example calculation of Free beta-hydroxyalkanoate (e.g. Free beta-hydroxypropionate) is set forth in the examples, below. Free beta-hydroxyalkanoate is indicative of the content of monomeric—3, 4, and 5 carbon beta-hydroxyalkanoic acid, monomeric—3, 4, and 5 carbon beta-hydroxyalkanoate salts, and combinations thereof, but not the content of beta-hydroxyalkanoate esters in a material being measured.

"Free beta-hydroxypropionate" refers to a measure of the monomeric 3 carbon beta-hydroxypropionic acid, monomeric 3 carbon beta-hydroxypropionate salts, and combinations thereof in a material, but not the beta-hydroxypropionate esters. It is measured as set forth above for free beta-hydroxyalkanoate.

"beta-Hydroxyalkanoate containing composition" is defined as a mixture of oligomers and esters of beta-hydroxyalkanoate, for example esters with saccharides, with monomeric beta-hydroxyalkanoate, and water. It is typically derived from beta-hydroxy carboxylic acid distillate recovery bottom streams, but may come from other sources as well.

"beta-Hydroxyalkanoate equivalents" is measured and determined using similar methods as those described for analyzing and determining total lactic acid (adjusted to account for all esters and expressed as free hydroxyalkanoic acid basis) in Holten, C. H. *Lactic Acid—Properties and Chemistry of Lactic Acid and Derivatives*, Verlag Chemie (1971): pp. 199-203. The esters of beta-hydroxyalkanoate with themselves and sacharides will be hydrolyzed in a similar manner to enable ready calculation of beta-hydroxyalkanoate equivalents. An example calculation of beta-Hydroxyalkanoate equivalents (e.g. beta-Hydroxypropionate equivalents) is set forth in the examples, below. Beta-Hydroxyalkanoate equivalents is indicative of the monomeric equivalents of beta-hydroxyalkanoate in the beta-hydroxyalkanoate containing composition whether in the form of monomers, oligomers, and/or esters with other compounds such as saccharides. For example, a dimeric beta-hydroxyalkanoate contains two beta-hydroxyalkanoate equivalents. As another example, a trimeric beta-hydroxyalkanoate contains three beta-hydroxyalkanoate equivalents. As another example, a saccharide esterified with one beta-hydroxyalkanoate contains one beta-hydroxyalkanoate equivalent, and a saccharide esterified with two beta-hydroxyalkanoate groups contains two beta-hydroxyalkanoate equivalents.

"beta-Hydroxypropionate containing composition" is defined as a mixture of oligomers and esters of beta-hydroxypropionate, for example esters with saccharides, with monomeric beta-hydroxypropionate, and water. It is typically derived from recovery bottom streams, but may come from other sources as well.

"beta-Hydroxypropionate equivalents" is defined as a measure of the monomeric equivalents of beta-hydroxypropionate in the beta-hydroxypropionate containing composition whether in the form of monomers, oligomers, and/or esters with other compounds such as saccharides. For example, a dimeric beta-hydroxypropionate contains two beta-hydroxypropionate equivalents. As another example, a trimeric beta-hydroxypropionate contains three beta-hydroxypropionate equivalents. As another example, a saccharide esterified with one beta-hydroxypropionate contains one beta-hydroxypropionate equivalent, and a saccharide esterified with two beta-hydroxypropionate groups contains two beta-hydroxyalkanoate equivalents. It is measured as set forth above for beta-hydroxyalkanoate equivalents.

"Overall recovery" is defined as the moles of ester of an alpha,beta-unsaturated carboxylic acid recovered at the end of the process divided by the moles of beta-hydroxyalkanoate equivalents in the beta-hydroxyalkanoate containing composition, multiplied by one hundred.

"Percent recovery" is defined as the moles of ester of an alpha-beta unsaturated carboxylic acid recovered at the end of the process divided by the moles of alkyl beta-hydroxyalkanoate in the reaction product, multiplied by one hundred.

"Percent yield" is defined as the moles of alkyl beta-hydroxyalkanoate in the reaction product divided by the moles of beta-hydroxyalkanoate equivalents in the beta-hydroxyalkanoate containing composition, multiplied by one hundred.

"Recovery bottom" is defined as the purge fraction remaining after the recovery of prime monomeric beta-hydroxycarboxylic acids by distillation or evaporation (or other methods known to one of skill in the art for recovering beta-hydroxycarboxylic acids. For example, liquid-liquid recovery using amine-based compounds).

"Saccharide equivalents" is defined as a measure of the monomeric equivalents of saccharides whether in the form of monosaccharides, disaccharides, oligosaccharides, and/or esters with other compounds, such as beta-hydroxycarboxylic acid. For example, a monosaccharide esterified with one or more beta-hydroxycarboxylic acids contains one saccharide equivalents. A disaccharide esterified with one or more beta-hydroxycarboxylic acids contains two saccharide equivalents. As another example, a sugar alcohol consists of one saccharide equivalent.

Producing an Ester of an Alpha,Beta-Unsaturated Carboxylic Acid from Beta-HydroxyCarboxylic Acid Recovery Bottoms In one preferred embodiment, the method comprises obtaining a beta-hydroxy carboxylic acid recovery bottom, such as the recovery bottoms obtainable from a plant manufacturing three carbon or four carbon beta-hydroxy carboxylic acids using an evaporative or distillation-based recovery system; combining a C1 to C6 mono-alcohol (preferably a C2 to C4 mono-alcohol) with the beta-hydroxy carboxylic acid recovery bottom to obtain a first mixture; heating the first mixture, optionally in the presence of a catalyst, to form a reaction product, distilling the reaction product and recovering a fraction comprising an ester of an alpha-beta unsaturated carboxylic acid.

The beta-hydroxycarboxylic acid recovery bottom typically comprises: at least 40 percent (%) by weight beta-hydroxyalkanoate equivalents (preferably, at least 50 wt % by weight beta-hydroxyalkanoate equivalents (for example, at least 55 wt %, at least 65 wt %, at least 75 wt %, at least 80 wt % by weight)); greater than 0.1 wt % by weight and no greater than about 50 wt % by weight free beta-hydroxyalkanoates (for example, from about 1 wt % to about 50 wt %, from about 3 wt % to about 40 wt %, from about 10 wt % to about 40 wt %, or from about 10 wt % to about 30 wt % free beta-hydroxyalkanoate, and typically less than 40 wt %, less than 35 wt %, and in some instances less than 30 wt %, for example, less than 25 wt % free beta-hydroxyalkanoate); at least 1% by weight saccharide equivalents; and less than 10% by weight water (for example, less than 8 wt %, less than 5 wt %, less than 3 wt %, less than 2 wt %, or less than 1 wt % water). The beta-hydroxyalkanoate typically is a three carbon or four carbon beta-hydroxycarboxylate, for example, 3-hydroxypropionate, 3-hydroxybutyrate, or 3-hydroxyisobutyrate.

The saccharide is typically a reducing sugar, for example, glucose, maltose, isomaltose, or combinations thereof, and may also include sugar alcohols, for example, polyols such as arabitol, glycerol, or combinations thereof.

The recovered fraction containing an ester of an alpha, beta-unsaturated carboxylic acid typically comprises: at least 50% by weight ester of an alpha,beta-unsaturated carboxylic acid (for example, at least 60 wt %, at least 70 wt %, at least 80 wt %, at least 90 wt %, at least 95 wt % and in some instances at least 99 wt % ester of an alpha,beta-unsaturated carboxylic acid; less than 1% by weight beta-hydroxycarboxylic acid, less than 3% by weight water (for example, less than 2 wt %, or less than 1 wt % water); and less than 0.5% by weight saccharide equivalents. Preferably, the ester of the alpha,beta-unsaturated carboxylic acid comprises an alkyl acrylate or an alkyl methacrylate.

Producing an Ester of an Alpha,Beta-Unsaturated Carboxylic Acid from a Beta-Hydroxyalkanoate Containing Composition In another embodiment, the method comprises producing an ester of an alpha,beta-unsaturated carboxylic acid from a beta-hydroxyalkanoate containing composition. The beta-hydroxyalkanoate containing composition preferably is derived from beta-hydroxycarboxylic acid recovery bottoms.

Hydroxyalkanoate Containing Composition

The hydroxyalkanoate containing composition typically comprises: the composition set forth above for the beta-hydroxy carboxylic acid recovery bottoms.

In some instances for the above embodiments, it may be desirable to have at least 1% by weight free beta-hydroxyalkanoate (for example, at least 5% by weight, at least 10% by weight, at least 15% by weight, or at least 20% by weight free hydroxyalkanoate), for example, when it is desirable to enhance the reaction rate of the esterification/transesterification reaction to form the reaction product.

The beta-hydroxyalkanoate typically comprises a 3-hydroxypropionate, 3-hydroxyisobutyrate, 3-hydroxybutyrate, and mixtures thereof.

The Mono-Alcohol

For all embodiments, mono-alcohol is typically combined with the beta-hydroxyalkanoate containing composition. The mono-alcohol is added in a molar ratio ranging typically from 1.1 to 1.0 to 10.0 to 1.0 (for example 1:1 to 5:1, from 1:1 to 3:1) of mono-alcohol to beta-hydroxyalkanoate equivalents present in the beta-hydroxyalkanoate containing composition. Typically, the mono-alcohol comprises C1 to C6 mono-alcohol. Preferably, the mono-alcohol comprises methanol, ethanol, propanol, or butanol. Due to their ready availability and the functional properties obtained in the unsaturated ester, ethanol and butanol are more preferred.

The First Mixture

For all embodiments, the first mixture is typically heated to form a reaction product. The first mixture is typically heated to a temperature ranging from 50 degrees Celsius (° C.) to 300° C. (for example, from 50° C. to 300° C., from 50° C. to 275° C., from 50° C. to 250° C., or from 50° C. to 200° C. In certain aspects, the first mixture is heated to a temperature from the reflux temperature of the first mixture at a given reaction pressure to 20° C. below the reflux temperature, for example from the reflux temperature of the first mixture at a given reaction pressure to 10° C. below the reflux temperature, or from the reflux temperature of the first mixture at a given reaction pressure to 5° C. below the reflux temperature of the first mixture at the given reaction pressure.

The pressure of the first mixture during the heating step typically ranges from 0.0 PSIG (i.e. 1 atmosphere) to 100 atmospheres (for example, from 5 atmospheres to 75 atmospheres, or from 10 atmospheres to 50 atmospheres). If a two-step reaction method is utilized (i.e. a heating step carried out to form a reaction product prior to a distillation step to dehydrate the alkyl beta-hydroxy alkanoate to an ester of an alpha,beta-unsaturated carboxylic acid and to recover the ester of the alpha,beta-unsaturated carboxylic acid), then the pressure during the first step is typically carried out from 14 PSIA (i.e. 1 atmosphere) to 265 PSIA (for example, from 14 PSIA to 215 PGIA, from 14 PSIA to 165 PSIA, from 14 to 140 PSIA, from 39 PSIA to 165 PSIA, from 39 PSIA to 140 PSIA, from 64 PSIA to 165 PSIA, and from 64 PSIA to 140 PSIA.

The method may be carried out in a single reactor in a single step, in a single reactor with multiple steps, or in several reactors. A two-step reaction method may be utilized in order to provide easy separation of excess water and/or mono-alcohol, before beginning to distill the reaction product from the first reaction to form and recover a fraction comprising an ester of the alpha,beta-unsaturated carboxylic acid. Removing excess water prior to the final distillation step is believed will result in improved conversion of the alkyl beta-hydroxyalkanoate to an ester of the alpha,beta-unsaturated carboxylic acid. Removing excess mono-alcohol will enhance the purity of the ester of the alpha,beta-unsaturated carboxylic acid.

Optionally, a catalyst may be used to assist in the formation of the reaction product during the heating step, while reducing the amount of heat that is applied and/or the temperature utilized. If a catalyst is used, typically the catalyst is an acid catalyst. Exemplary catalysts include solid acid catalysts, Bronsted acid catalysts, Lewis acid catalysts, or combinations thereof.

In one aspect, the catalyst comprises sulfuric acid, and the initial amount of catalyst present ranges from 0.01 to 5% by weight of the beta-hydroxyalkanoate containing composition in the first mixture, and more preferably ranges from 0.1 to 3% by weight of the beta-hydroxyalkanoate containing composition, and even more preferably ranges from 0.5 to 2% by weight of the beta-hydroxyalkanoate containing composition.

An alternative to using a catalyst is to run the reaction in the absence of a catalyst. Without being bound by theory, it is believed that under such conditions the reaction proceeds as an autocatalyzed reaction, wherein the acid groups in the beta-hydroxyalkanoate (e.g., 3-hydroxypropionic acid) composition are sufficient to catalyze the esterification/transesterification reactions. A particular advantage of this alternative aspect is that it significantly reduces the alkali utilized, if pH adjustment is carried out prior to distillation (optional pH adjustment step discussed below), and also reduces the water introduced by the aqueous alkali, as well as water that is formed during neutralization. In this alternative aspect, however, it may be necessary to run the reaction at a higher temperature and pressure (when compared to catalyzed reactions) to achieve the desired yields in a reasonable period of time.

Optional Neutralizing/pH Adjustment Step

For all embodiments, an optional neutralizing/pH adjustment step may be carried out before distillation. In this step, a basic compound is added to adjust the pH to the desired level. The desired pH typically will vary from 3 to 7.5, for example from 4.0 to 6.5, from 4.0 to 6.0. In some instances it may be desirable to obtain a pH of from 6.5 to 7.5 prior to distillation.

Optional High Boiling Solvent Addition

For all embodiments, optionally, a high boiling solvent, for example but not limited to glycerol, may be added to the reaction product (after the reaction to form the first mixture), before the distillation step.

Optional Alpha-Beta-Unsaturated Carboxylic Acid Antipolymerization Agent

For all embodiments, optionally, an antipolymerization agent may be added during the heating step where acrylate formation is likely to occur. For a multistep reaction, the antipolymerization agent preferably is added after the esterification/transesterification reaction is substantially complete. Typically the antipolymerization agent is added prior to and/or during distillation to inhibit oligomerization of alpha,beta-unsaturated carboxylic acids and esters of alpha, beta-unsaturated carboxylic acids. Antipolymerizations agents that can be utilized are known to one of skill in the art. For example, a monomethyl ether of hydroquinone ("MHQ") or Phenothiazine may be added. Typically, the amount added will be from about 10 ppm to 10,000 ppm (for example from 50 ppm to 500 ppm). The antipolymerization agent typically is added before or during the heating of the first reaction product if a single step reaction method is utilized and after the formation of the reaction product from the first mixture and prior to or during the distillation step if a two-step reaction is utilized.

Distilling the Reaction Product

For all embodiments, the reaction product comprising the alkyl beta-hydroxyalkonoate is typically either: (i) concurrently distilled and converted to the ester of an alpha,beta-unsaturated acid in a single step; or (ii) formed first and subsequently distilled and converted to the ester of an alpha,beta-unsaturated carboxylic acid in a multistep method. The recovered ester of an alpha,beta-unsaturated carboxylic acid comprises the composition of the recovered ester of an alpha,beta-unsaturated carboxylic acid recovered from the process set forth for producing such an ester of an alpha,beta-unsaturated carboxylic acid from a beta-hydroxy carboxylic recovery bottoms, described above.

If a single-step reaction method is utilized, fractional distillation or a series of separation/recovery steps may be utilized to recover the fraction enriched in the ester of an alpha,beta-unsaturated carboxylic acid.

If a multi-step reaction method is utilized, it is preferable to maintain the temperature of the first reaction (i.e. conversion of the first mixture to an alkyl beta-hydroxyalkanoate) at a lower temperature (e.g. less than 160° C., less than 150° C., less than 140° C., less than 130° C., less than 120° C.) than the temperature utilized for distillation and/or conversion of the alkyl beta-hydroxyalkanoate to the ester of an alpha,beta-unsaturated carboxylic acid (e.g. greater than 120° C., for example, at least 130° C., at least 140° C., at least 150° C., at least 160° C.). Typically, water and/or excess unreacted mono-alcohol will be removed prior to or during distillation to enhance the formation and recovery of the ester of an alpha,beta-unsaturated carboxylic acid. Evaporative heating and/or distillation may be utilized to recover the final product during this distillation step. Examples of methods that may be utilized include fractional distillation apparatus, simple distillation apparatus and evaporators. The types of evaporators that may be utilized include forced circulation evaporators, boiling tube evaporators, wiped film evaporators, rising film evaporators, climbing evaporators, and other distillation methods known to one of skill in the art.

In the distillation processes described above, a reduced pressure typically below atmospheric pressure is used to recover the ester of an alpha,beta-unsaturated carboxylic acid fraction. In certain aspects, the pressure of the distillation step may range from 0.1 torr to 750 torr, 0.1 torr to 200 torr, 0.1 torr to 100 torr, and more specifically 0.5 torr to 100 torr.

Percent Yield, Percent Recovery & Overall Recovery

For all embodiments, the percent yield is typically greater than 50%, for example, greater than 60%, greater than 70%, greater than 80%, greater than 90%, and more preferably greater than 95%. The percent recovery is typically greater than 50%, for example, greater than 60%, greater than 70%, greater than 80%, greater than 90%, and, more preferably greater than 95%. The overall recovery is typically greater than 30%, for example greater than 40%, greater than 50%, greater than 60%, greater than 70%, and in some instances greater than 80%, for example greater than 85%.

Methods

The following methods described further below are used in the various examples and are presented to illustrate the present invention and to assist one of ordinary skill in making and using the same. The methods are not intended in any way to otherwise limit the scope of the invention.

Method for Calculating Free Alkanoates and Alkanoate Equivalents:

The amount of free beta-hydroxyalkanoate and beta-hydroxyalkanoate equivalents present in the beta-hydroxyalkanoate containing composition are measured and determined in accordance with the following:

The free beta-hydroxyalkanoate and total beta-hydroxyalkanaote content in beta-hydroxyalkanoate containing compositions is determined by a titration method similar to the method described in the Holten reference mentioned above. "Bound" beta-hydroxyalkanoate is the beta-hydroxyalkanoate that is in the form of esters and is calculated as shown below. Beta-Hydroxyalkanoate equivalents can then be calculated from the free and bound beta-hydroxyalkanoates.

Free beta-hydroxyalkanoate=$J$ % by weight (J is similar to the free acidity, i.e., a, in the Holten reference)

Total beta-hydroxyalkanoate=$K$ % by weight (K is similar to the total lactic acid, i.e., a+b, in the Holten reference)

Bound beta-hydroxyalkanoate=$(K-J)$% by weight

Beta-Hydroxyalkanoate Equivalents=$J+[(K-J) \times C]$%

(where "C" for 3 carbon beta-hydroxyalkanoates is 90/72; where "C" for 4 carbon beta-hydroxyalkanoates is 104/86; where "C" for 5 carbon beta-hydroxyalkanoates 118/100)

EXAMPLES

The following examples are presented to illustrate the present invention and to assist one of ordinary skill in making and using the same. The examples are not intended in any way to otherwise limit the scope of the invention.

Example 1: Synthesis of Ethyl 3-hydroxypropionate ("3-HP ethyl ester") Using 3-Hydroxypropionic Acid Recovery Bottoms Ultra High Performance Liquid Chromatography (UHPLC) Method for the Analysis of Ethyl 3-Hydroxypropionate:

This method is used to analyze the content of Ethyl 3-hydroxypropionate in reaction mixtures. Approximately 1 gram of sample is weighed into a 50 mL volumetric flask. The analyte is extracted with 50 ml acetonitrile by sonication for 5 minutes. The solution is transferred to a 50 mL centrifuge tube and centrifuged at 3000 rpm for 3 minutes. The supernatant is removed for analysis via UHPLC as follows.

Chromatographic separation: 1 µL of the extraction solution is injected onto either a Waters Acquity UPLC or Agilent 1290 UHPLC. Separation of analytes is performed on a Waters Acquity HSS T3 C18, 2.1 mm×100 mm, 1.8 µm analytical column. The column is maintained at 30° C. A mobile phase gradient is used where mobile phase A is 0.1% formic acid and mobile phase B is acetonitrile, the phase gradient is outlined in the following table. The retention time for ethyl 3-HP is 2.2 minutes. Quantification of Ethyl 3-hydroxypropionate is performed by applying the peak area of the test sample directly to areas for a set of standards measured by UV at 210 nm.

TABLE 1

Gradient elution for Ethyl 3-hydroxypropionate

| Time (min) | Flow Rate (mL/min) | % A | % B |
|---|---|---|---|
| Initial | 0.6 | 97.0 | 3.0 |
| 0.5 | 0.6 | 97.0 | 3.0 |
| 2.5 | 0.6 | 82.0 | 18.0 |
| 3.0 | 0.6 | 5.0 | 95.0 |
| 3.5 | 0.6 | 5.0 | 95.0 |
| 4.0 | 0.6 | 97.0 | 3.0 |
| 5.5 | 0.6 | 97.0 | 3.0 |

Reaction of 3-Hydroxypropionic Acid Recovery Bottoms ("3-HPRB") with Ethanol ("EtOH"):

Recovery bottoms from a 3-Hydroxypropionic acid (3-HP) manufacturing process that utilizes a distillation process for recovering 3-hydroxypropionic acid are obtained having a composition as detailed in the Table 2 below are mixed with ethanol (200 proof) at mass ratios of 50:50, 40:60 or 30:70 of 3-HPRB to ethanol. 98% sulfuric acid at 1 to 4% by weight relative to the 3-HPRB is added as a catalyst to the reaction mixture. The reaction mixture is constantly stirred and heated to a temperature of 78-80° C. under atmospheric pressure. The reaction mixture is held at this temperature for 6 to 14 hours, after which it is cooled to room temperature and analyzed by UHPLC. The composition of the resulting reaction product is detailed in Table 3.

TABLE 2

(3-HPRB Composition)

| Compound | Weight Percent (wt %) |
|---|---|
| 3-Hydroxypropionate Equivalents | 66.74 wt % |
| Free 3-Hydroxypropionate | 11.53 wt % |
| Saccharide Equivalents | >1 wt % |
| Water | >0.1 wt % |

TABLE 3

| Reaction mixture (Mass ratio) | Reaction time (hrs) | Total weight of reaction mixture (g) | Yield of 3-HP ethyl ester (%) |
|---|---|---|---|
| 3-HPRB:EtOH (50:50) - 6 hr., 1 wt % H2SO4 | 6 | 108.47 | 56.14 |
| 3-HPRB:EtOH (50:50) - 6 hr., 2 wt % H2SO4 | 6 | 112.95 | 52.97 |
| 3-HPRB:EtOH (50:50) - 6 hr., 3 wt % H2SO4 | 6 | 103.85 | 50.81 |

TABLE 3-continued

| Reaction mixture (Mass ratio) | Reaction time (hrs) | Total weight of reaction mixture (g) | Yield of 3-HP ethyl ester (%) |
|---|---|---|---|
| 3-HPRB:EtOH (50:50) - 6 hr., 4 wt % H2SO4 | 6 | 99.62 | 48.38 |
| 3-HPRB:EtOH (50:50) - 6 Hr., 3 wt % H2SO4 | 6 | 113.60 | 51.74 |
| 3-HPRB:EtOH (40:60) - 6 Hr., 3 wt % H2SO4 | 6 | 112.65 | 60.54 |
| 3-HPRB:EtOH (30:70) - 6 Hr., 3 wt % H2SO4 | 6 | 106.73 | 66.75 |
| 3-HPRB:EtOH (30:70) - 8 Hr., 3 wt % H2SO4 | 8 | 112.37 | 66.34 |
| 3-HPRB:EtOH (30:70) - 10 Hr., 3 wt % H2SO4 | 10 | 122.33 | 67.24 |
| 3-HPRB:EtOH (30:70) - 14 Hr., 3 wt % H2SO4 | 14 | 112.44 | 65.12 |

The results in Table 3 show that no large differences in yield are observed with an increase in catalyst concentration. Further, increasing the ethanol content relative to the 3-HIP recovery bottoms from 50:50 to 70:30 increases the yield of 3-Hydroxypropionic acid ethyl ester (i.e. Ethyl 3-hydroxypropionate) and increasing the time of the reaction beyond 6 hours at a 3-HPRB to ethanol ratio of 3:7 did not increase the yield. i.e., the reaction appears to reach equilibrium in about 6 hours.

Gas Chromatography (GC) analysis of Butyl-3-hydroxypropionate (3-Hydroxypropionic acid butyl ester), Butyl acrylate, and n-butanol in reaction mixtures utilized for Examples 2 and 3, below:

The GC instrument is an Agilent 7890 Gas Chromatograph with split/splitless injector and flame ionization detector. The column is an Agilent HP-5 column (length=25 m, i.d.=0.2 mm, film=0.5 μm). Initial oven temperature is 50° C., held for 3.0 min, then a 15° C./min ramp up to 325° C., and held there for 8.67 min, for a total run time of 30 min. Inlet Temperature at 275° C., with Hydrogen as the carrier gas at a constant flow of 0.5 mL/min. The flame ionization detector temperature is 275° C., with Hydrogen (40 mL/min) as the fuel.

200 mg of the test material is diluted with 20 mL of GC grade Acetonitrile in a scintillation vial. The vial is capped and mixed thoroughly by sonication. 1.5 mL of the solution is filtered through a 0.2 μm filter, and transferred to a GC vial with a Teflon-lined cap. Sample injection volume is 1.0 μL.

The retention times of n-butanol, butyl acrylate, and butyl-3-hydroxypropionate are approximately 4.04 min, 7.67 min, and 12.72 min respectively. The concentrations of n-butanol and butyl acrylate in the reaction mixtures are determined based on peak intensities compared with individual standard curves generated with high purity n-butanol and butyl acrylate. The concentration of butyl-3-hydroxypropionate in the reaction mixtures is determined based on peak intensities compared with individual standard curves generated with high purity tert-butyl-3-hydroxypropionate.

Example 2: Synthesis of Butyl 3-Hydroxypropionate and Butyl Acrylate from 3-Hydroxypropionic Acid Recovery Bottoms ("3-HPRB2")

Recovery bottoms from a 3-Hydroxypropionic acid (3-HP) manufacturing process that utilizes a distillation process for recovering 3-hydroxypropionic acid (100.48 grams) are obtained having a composition detailed in the Table 4 ("3-HPRB2") below is mixed with 1-butanol (233.13 grams) (Sigma Aldrich, purity≥99.7%) at the mass ratio of 30:70 of 3-HPRB2 to 1-butanol. Monomethyl ether of Hydroquinone (MHQ) is added to reaction mixture to obtain a 200 ppm concentration in the reaction. 93% sulfuric acid (5.09 grams) at 1.44% by weight relative to the total reaction mass is added as the catalyst to the reaction mixture. The reaction mixture is continuously stirred and heated to a temperature of 118-120° C. under atmospheric pressure. The reaction mixture is held at this temperature for 8 hours, and every two hours the reaction mixture is sampled and the ester content determined by Gas Chromatography and moisture content (i.e. water content) determined by Karl Fisher titration. A Dean-Stark trap with a dual stopcock is attached to the flask and water is removed overhead as an azeotrope with 1-butanol. The water that separates from the azeotrope is drained from the trap and the 1-butanol is recycled back into the flask. This is repeated throughout the entire reaction trial. The separated water stream is collected in a 20 ml scintillation vial. The reaction analysis of the composition of the reaction mixture is shown in Table 5.

TABLE 4

Compositional analysis of 3-HPRB2

| Compound | Weight Percent (wt %) |
|---|---|
| 3-Hydroxypropionate Equivalents | 81.64 wt % |
| Free 3-Hydroxypropionate | 44.73 wt % |
| Saccharide Equivalents | >1 wt % |
| Water | >0.1 wt % |

Results:

TABLE 5

Analytical breakdown of the individual samples collected throughout reaction 1
Reaction 1

| Sample | Moisture (%) | Butyl-3-hydroxypropionate (% in Rxn mixture) | Yield (%) | Butyl Acrylate (% in Rxn Mixture) | Yield (%) |
|---|---|---|---|---|---|
| 0 hr | 2.50 | 0.00 | 0.00 | 0.51 | 1.49 |
| 2 hr | 2.68 | 0.44 | 1.11 | 0.76 | 2.18 |
| 4 hr | 1.62 | 1.66 | 4.10 | 0.78 | 2.21 |
| 6 hr | 1.45 | 2.73 | 6.68 | 0.92 | 2.56 |
| 8 hr | 1.29 | 3.93 | 9.49 | 1.10 | 3.02 |

Example 3

3-HPRB2 (100.38 grams) is mixed with 1-butanol (233.63 grams) at the mass ratio of 30:70 of 3-HPRB2 to 1-butanol. MHQ is added to reaction mixture to obtain a 200 ppm concentration in the reaction. 93% sulfuric acid (18.10 grams) at 5% by weight relative to the total reaction mass is added as the catalyst to the reaction mixture. The reaction mixture is continuously stirred and initially heated to a temperature of 118-120° C. under atmospheric pressure and then the temperature systematically increased throughout the 9 hour reaction. The reaction mixture is sampled every two hours and the ester content determined by Gas Chromatography and moisture content determined by Karl Fisher titration. A Dean-Stark trap with a dual stopcock is attached to the flask and the water removed overhead as an azeotrope with butanol. The water that separates from the azeotrope is drained from the trap and the butanol recycled back into the flask. This is repeated throughout the entire reaction trial. The separated water stream is collected in two 20 ml scintillation vials. In example 3, the distillation head is thermally insulated and the distillation head temperature is controlled at 117° C.
Results:

TABLE 6

Analytical breakdown of the individual samples collected throughout reaction 2.
Reaction 2

| Sample | Reaction Temp (° C.) | Moisture (%) | Butyl-3-hydroxy-propionate (% in Rxn mixture) | Yield (%) | Butyl Acrylate (% in Rxn Mixture) | Yield (%) |
|---|---|---|---|---|---|---|
| 0 hr | 116.0 | 2.97 | 0.00 | 0.00 | 0.46 | 1.38 |
| 2 hr | 121.3 | 2.09 | 5.76 | 14.79 | 1.34 | 3.92 |
| 4 hr | 124.3 | 1.42 | 13.45 | 33.53 | 2.33 | 6.60 |
| 6 hr | 127.6 | 1.06 | 22.46 | 54.05 | 3.76 | 10.32 |
| 8 hr | 134.2 | 0.59 | 30.41 | 70.73 | 7.06 | 18.72 |
| 9 hr | 138.0 | 0.35 | 33.69 | 72.17 | 8.20 | 21.29 |

Table 6 shows that 3-hydroxypropionic acid distillation bottoms (i.e. a beta-hydroxyalkanoate recovery bottom) comprising monomers and oligomers of 3-hydroxypropionic acid (a beta-hydroxyalkanoate), saccharide equivalents, and water can be readily converted to butyl acrylate in a single step reaction method. While not shown, it is believed that even higher yields of butyl acrylate can be obtained by using a multistep reaction method. Various monoalcohols and beta-hydroxyalkanoates can be utilized.

What is claimed is:

1. A method for producing an ester of acrylic acid, comprising:
   a) obtaining 3-hydroxypropionic acid recovery bottoms;
   b) mixing a mono-alcohol with the recovery bottoms to obtain a first mixture;
   c) heating the first mixture comprising 3-hydroxypropionate to form a reaction product; and
   d) distilling the reaction product and recovering an ester of acrylic acid fraction.

2. The method of claim 1, wherein the recovery bottom comprises:
   i) at least 40 percent by weight 3-hydroxypropionate equivalents;
   ii) from 0.1 percent by weight to 50 percent by weight free 3-hydroxypropionate;
   iii) at least 1 percent by weight saccharide equivalents; and
   iv) less than 5 percent by weight water.

3. The method of claim 1, wherein the ester of the acrylic acid fraction comprises:
   i) at least 80 percent by weight of the ester of acrylic acid;
   ii) less than 1 percent by weight 3-hydroxypropionic acid;
   iii) less than 1 percent by weight water; and
   iv) less than 0.5 percent by weight saccharide equivalents.

4. The method of claim 1, wherein the recovery bottom comprises 3-hydroxypropionic acid or 3-hydroxypropionate.

5. The method of claim 1, wherein the ester of the acrylic acid comprises alkyl acrylate or mixtures thereof.

6. The method of claim 1, wherein step (d) comprises dehydrating a 3-hydroxypropionate to form an ester of acrylic acid.

7. The method of claim 1, wherein step (c) is carried out in the presence of a catalyst.

8. The method of claim 7, wherein the catalyst is a solid acid catalyst, a Bronsted acid, or a Lewis acid.

9. The method of claim 7, wherein the catalyst is sulfuric acid, and the initial amount of catalyst present is from about 0.01 to about 5 percent by weight of the 3-hydroxypropionate containing composition.

10. The method of claim 7, wherein the catalyst is sulfuric acid, and the initial amount of catalyst present is from about 0.5 to about 2 percent by weight of the 3-hydroxypropionate containing composition.

11. The method of claim 1, wherein an acrylate anti-polymerization agent is added prior to or during the method.

12. The method of claim 11, wherein the acrylate anti-polymerization agent is added prior to or during step (d).

13. The method of claim 11, wherein the acrylate anti-polymerization agent is added prior to or during step (c).

14. The method of claim 13, wherein the antipolymerization agent is present at from 10 ppm to 10,000 ppm.

15. The method of claim 6, wherein prior to the dehydrating of step (d), the water content is less than 2 wt %.

16. The method of any one of claims 1-4, 5-9, 10-13, 14, and 15, wherein the temperature during the dehydrating of step (d) is at least 120° C.

17. The method of claim 6, wherein after step (c) and prior to the dehydrating of step (d) mono-alcohol and water are removed.

18. The method of claim 6, wherein the temperature during step (c) is less than 130° C.

19. The method of claim 1, wherein the ester of acrylic acid fraction recovered in step (d) comprises at least 50 percent by weight ester of the acrylic acid.

* * * * *